(12) United States Patent
Matsushima et al.

(10) Patent No.: US 11,051,904 B2
(45) Date of Patent: Jul. 6, 2021

(54) MARKER FOR USE IN LIVING BODY AND INSTRUMENT SET FOR INSERTING MARKER FOR USE IN LIVING BODY

(71) Applicant: NIPPON PISTON RING CO., LTD., Saitama (JP)

(72) Inventors: Hiroshi Matsushima, Saitama (JP); Takasumi Kubo, Saitama (JP); Yuki Kimura, Saitama (JP); Yoshiki Ishikawa, Saitama (JP); Takashi Kawabata, Saitama (JP)

(73) Assignee: NIPPON PISTON RING CO., LTD.

( * ) Notice: Subject to any disclaimer, the term of this patent is extended or adjusted under 35 U.S.C. 154(b) by 179 days.

(21) Appl. No.: 16/078,078

(22) PCT Filed: Feb. 23, 2017

(86) PCT No.: PCT/JP2017/006837
§ 371 (c)(1),
(2) Date: Aug. 21, 2018

(87) PCT Pub. No.: WO2017/146149
PCT Pub. Date: Aug. 31, 2017

(65) Prior Publication Data
US 2019/0008605 A1 Jan. 10, 2019

(30) Foreign Application Priority Data
Feb. 26, 2016 (JP) .............................. JP2016-034953

(51) Int. Cl.
*A61B 90/00* (2016.01)
*A61B 6/12* (2006.01)

(52) U.S. Cl.
CPC ................ *A61B 90/39* (2016.02); *A61B 6/12* (2013.01); *A61B 2090/3904* (2016.02); *A61B 2090/3908* (2016.02); *A61B 2090/3954* (2016.02); *A61B 2090/3966* (2016.02); *A61B 2090/3987* (2016.02); *A61B 2090/3991* (2016.02)

(58) Field of Classification Search
CPC ................ A61B 90/39; A61B 90/3991; A61B 2090/3904; A61B 2090/3908; A61B 2090/3912; A61B 2090/3937; A61B 2090/3966; A61B 2090/3987; A61B 2090/3954; A61B 2090/3991
See application file for complete search history.

(56) References Cited

U.S. PATENT DOCUMENTS

| 6,752,154 B2 * | 6/2004 | Fogarty | A61B 90/39 128/899 |
| 2004/0168692 A1 | 9/2004 | Fogarty et al. | |
| 2013/0309518 A1 * | 11/2013 | Takeguchi | A61L 27/06 428/544 |

FOREIGN PATENT DOCUMENTS

| JP | H02-094556 U | 7/1990 |
| JP | 2011-083625 A | 4/2011 |

* cited by examiner

*Primary Examiner* — Carrie R Dorna
(74) *Attorney, Agent, or Firm* — Harness, Dickey & Pierce, P.L.C.

(57) ABSTRACT

A marker for use in a living body includes an indicator part to be placed in a living body for a predetermined period of time, and the indicator part is configured to indicate information on the living body or information on the indicator part by means of a difference in X-ray image. Thus, there are provided the marker for use in a living body and an instrument set for inserting the marker for use in a living body capable of identifying a predetermined site in a living body easily and accurately.

4 Claims, 13 Drawing Sheets

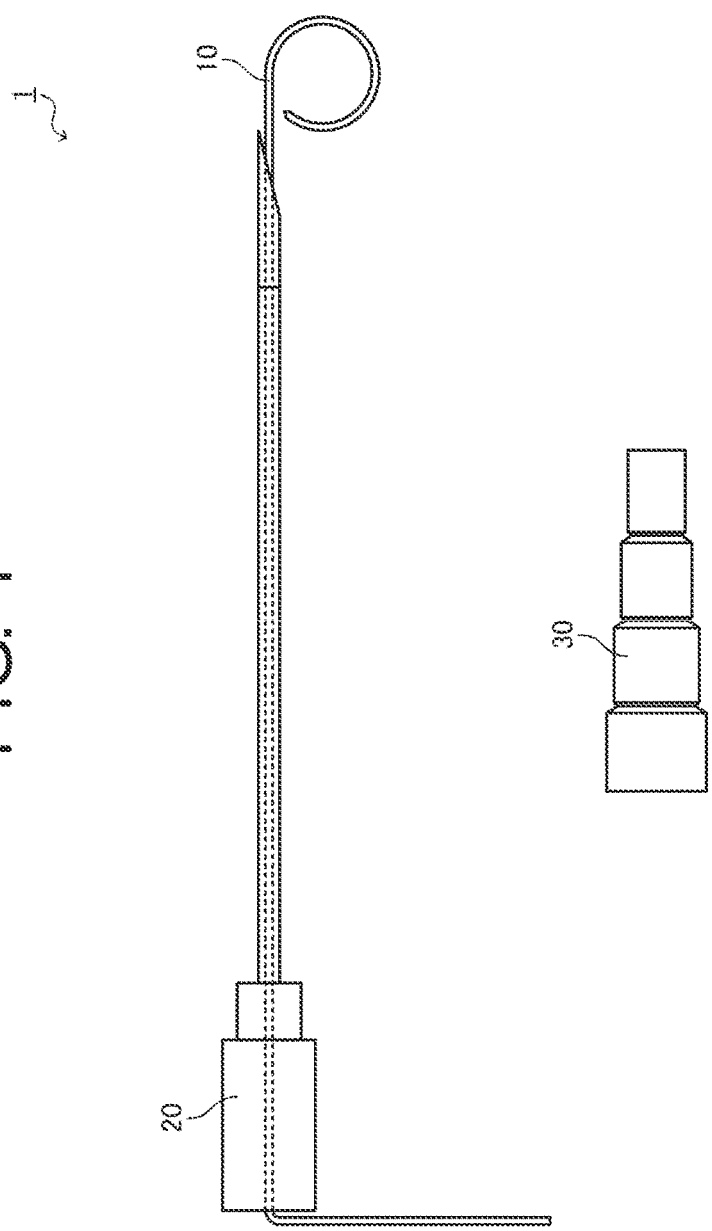

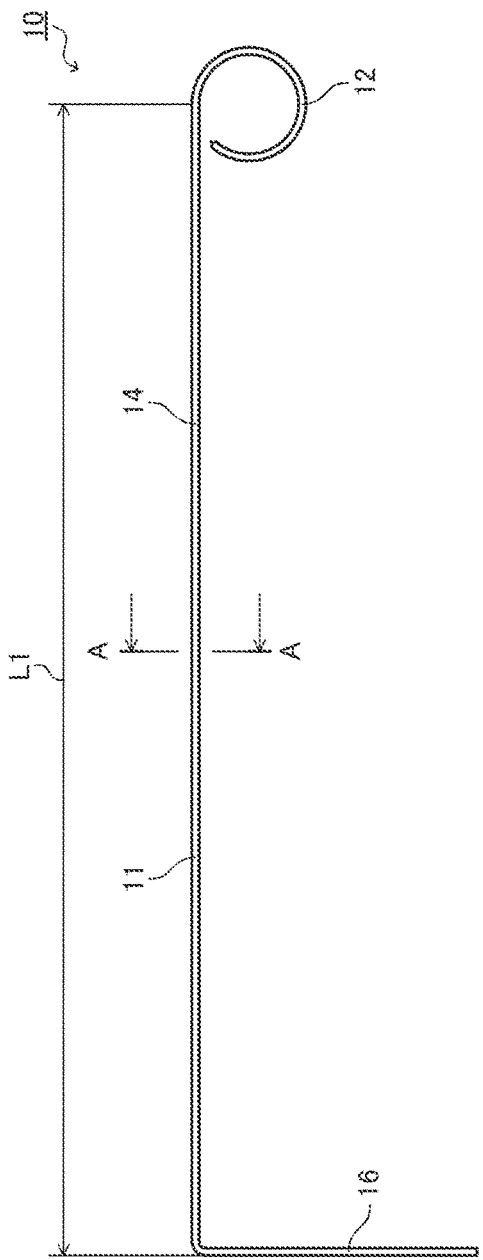
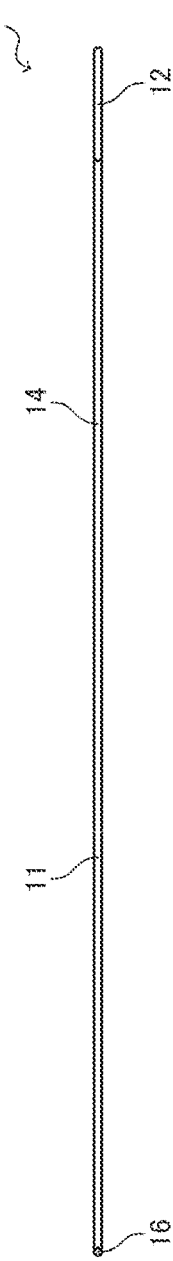
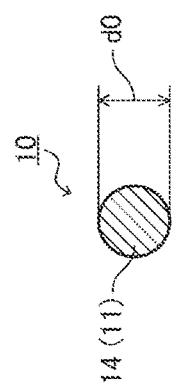
FIG. 2A
FIG. 2B
FIG. 2C

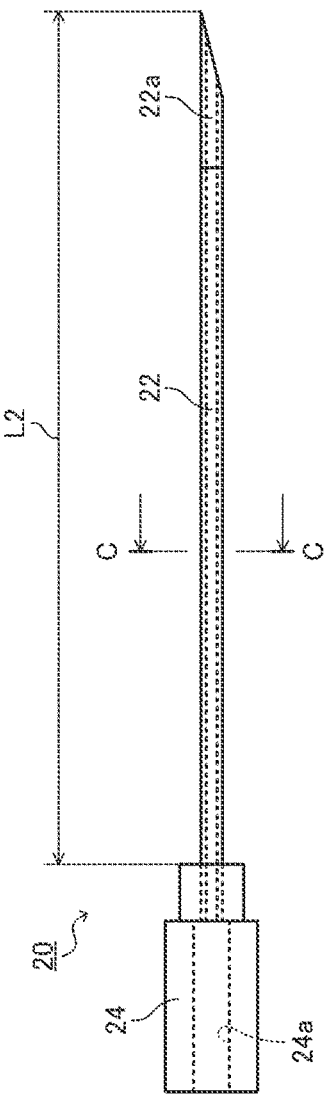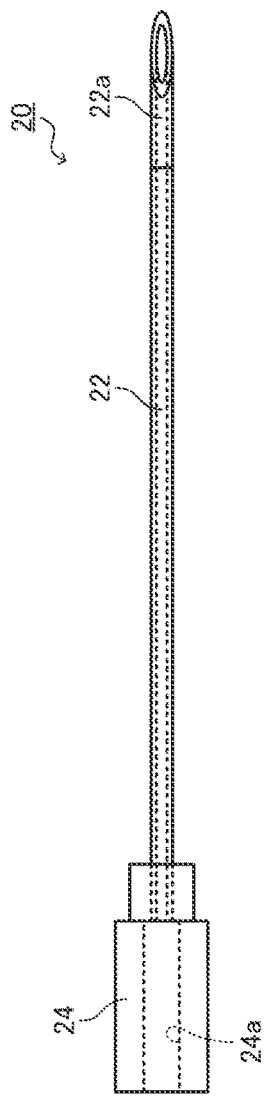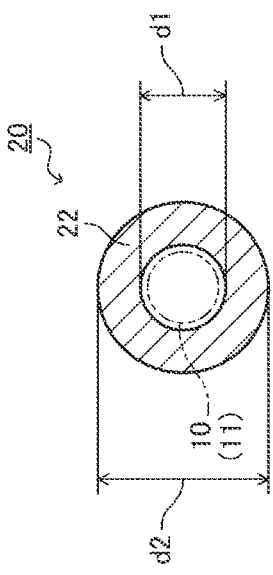

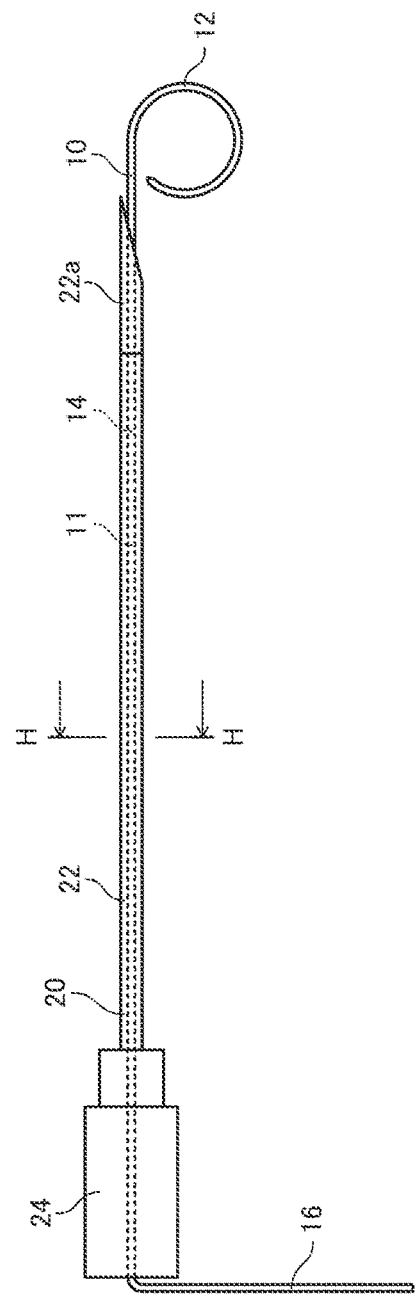
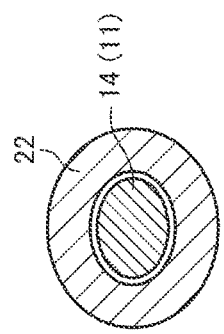
FIG. 11A
FIG. 11B

MARKER FOR USE IN LIVING BODY AND INSTRUMENT SET FOR INSERTING MARKER FOR USE IN LIVING BODY

CROSS-REFERENCE TO RELATED APPLICATIONS

This application is a U.S. National Stage Application of International Application No. PCT/JP2017/006837, filed on Feb. 23, 2017, and published in Japanese as WO 2017/146149 on Aug. 31, 2017 and claims priority to Japanese Application No. 2016-034953, filed on Feb. 26, 2016, the entire disclosures of the above applications are incorporated herein by reference.

BACKGROUND

Technical Field

The present invention relates to a marker for use in a living body that is placed in a living body as an indicator for cancer tissue or a lesion, for example, and an instrument set for inserting a marker for use in a living body that is configured to place the marker for use in a living body in the living body.

Related Art

Along with technical progress such as magnetic resonance imaging (MRI) or computed tomography (CT), new methods for cancer screening have been developed and proposed in recent years. As a result, various cancers have become detectable in early stages. If cancer tissue is found in cancer screening, the injection of a dye, such as indigocarmine, or the placement of a hook wire made of a stainless steel, for example, is generally performed in advance while checking the cancer tissue through an X-ray CT image or the like, in order to provide a marker (indicator) at the site. At a later date, surgery to remove the cancer tissue is performed on the basis of the indicator.

The dye such as indigocarmine, however, spreads as time passes. Thus, it may be difficult to identify the cancer tissue at the time of surgery, thus requiring larger excision. Since the hook wire is formed by bending a tip portion of a stainless steel wire in a V-shape, a degree of invasiveness to a living body is high.

Specifically, the hook wire is inserted into an injection needle while being folded with the V-shaped tip portion being elastically deformed. After the injection needle is inserted into the living body, the tip portion of the hook wire is projected from a tip of the injection needle to be deployed in the V-shape. The hook wire is left in place in the living body by withdrawing the injection needle lastly. Therefore, a thick injection needle having an inner diameter at least more than double the diameter of the stainless steel wire is required for the insertion of the hook wire. Furthermore, it is difficult for the stainless steel wire to have a small wire diameter due to its property of being plastically deformed relatively easily. These lead to a high degree of invasiveness to the living body.

To cope with this problem, a contrast material for medical use that can reduce a degree of invasiveness to a living body and can accurately identify the position of cancer tissue and the like through the use of a nickel-titanium (Ni—Ti)-based shape memory alloy has been proposed (see Japanese Utility Model Application Laid-Open Publication No. Hei. 2-94556, for example).

By using such a shape memory alloy as a material of a wire, a tip portion of the wire, which has memorized a shape (bent state) beforehand, is straightened temporarily and then inserted into an injection needle. Thereafter, the tip portion can be returned to its original shape in a living body. This allows for the use of a relatively thin injection needle. Furthermore, the diameter of the wire can be reduced since the wire is less likely to have plastic deformation while allowing for flexible elastic deformation due to its superelasticity. Since a degree of freedom in the shape of the tip portion of the wire is increased, an indicator can be provided so as to surround cancer tissue and the like by producing a C-shape memory tip portion, for example. Thus, the position of the cancer tissue and the like can be identified accurately.

Such a nickel-titanium-based alloy, however, has a low X-ray absorptivity, thus resulting in a low contrast property in X-ray photography by CT and the like. To place the wire in the living body through the use of the injection needle, the positioning of the wire needs to be performed while checking the X-ray image. However, since the visibility of the wire in the image is low, the accurate positioning of the wire requires skills. Moreover, when the position of the tip portion of the wire is identified by means of an X-ray image at the time of future surgery or during a follow-up, it may take some time to find such a position.

Furthermore, since such a nickel-titanium-based alloy has a strong magnetic property, there is a possibility of causing problems, such as producing artifacts in the image or generating heat in the wire due to a magnetic field generated by an MRI machine, when a diagnosis by the MRI is performed with the wire being left in place in the living body.

In view of such circumstances, it is an object of the present invention to provide a marker for use in a living body and an instrument set for inserting the marker for use in a living body capable of identifying a predetermined site in a living body easily and accurately.

SUMMARY OF THE INVENTION (1) The present invention provides a marker for use in a living body including an indicator part to be placed in a living body for a predetermined period of time, in which the indicator part is configured to indicate information on the living body or information on the indicator part by a difference in X-ray image.

(2) The present invention further provides the marker for use in a living body according to (1) described above in which at least a part of the indicator part is constituted by a titanium alloy that has an X-ray absorptivity higher than that of a stainless steel and a magnetic property lower than that of a platinum-tungsten alloy.

(3) The present invention further provides the marker for use in a living body according to (2) described above in which the titanium alloy has an elastic limit of not lower than 2% and not higher than 6%.

(4) The present invention further provides the marker for use in a living body according to (2) or (3) described above in which the titanium alloy contains tantalum.

(5) The present invention further provides the marker for use in a living body according to (2) or (3) described above in which the titanium alloy contains tantalum and tin.

(6) The present invention further provides the marker for use in a living body according to any one of (2) to (5) described above in which the indicator part is formed by bending a line body comprising the titanium alloy in a predetermined shape.

(7) The present invention further provides the marker for use in a living body according to (6) described above in which the indicator part has a shape satisfying a relationship of R>50×W/ε1 where R [mm] denotes a radius of curvature of a bent portion of the line body, W [mm] denotes a dimension of the line body in a direction of the radius of curvature, and ε1 [%] denotes an elastic limit of the titanium alloy.

(8) The present invention further provides the marker for use in a living body according to (6) or (7) described above in which the indicator part is formed in an unclosed ring shape or in a helical shape capable of surrounding a circular region having a diameter of not smaller than 3 mm and not larger than 10 mm.

(9) The present invention further provides the marker for use in a living body according to any one of (6) to (8) described above, including a transporting part formed by the line body having a generally linear shape that is continuous with the indicator part.

(10) The present invention further provides the marker for use in a living body according to (9) described above, including an orientation indicating part provided in the transporting part, the orientation indicating part being configured to indicate an orientation of the indicator part relative to the transporting part.

(11) The present invention further provides the marker for use in a living body according to (10) described above in which the orientation indicating part is formed by bending the line body.

(12) The present invention further provides the marker for use in a living body according to any one of (6) to (11) described above in which the line body has a cross-sectional shape having a longitudinal direction.

(13) The present invention further provides an instrument set for inserting a marker for use in a living body, including: the marker for use in a living body according to any one of (1) to (12) described above; and a dispenser configured to insert the marker for use in a living body into a living body, in which the dispenser includes a tubular guide part configured to house the indicator part so as to be movable in an axial direction thereof.

(14) The present invention further provides an instrument set for inserting a marker for use in a living body, including: the marker for use in a living body according to any one of (6) to (12) described above; and a dispenser configured to insert the marker for use in a living body into a living body, in which the dispenser includes a tubular guide part configured to house the indicator part such that the indicator part is movable in an axial direction while the indicator part is deformed into a generally linear shape.

(15) The present invention further provides the instrument set for inserting a marker for use in a living body according to (14) described above in which the line body and the guide part have shapes configured to restrict a relative rotation of the marker for use in a living body and the guide part about the axial direction of the guide part.

(16) The present invention further provides the instrument set for inserting a marker for use in a living body according to (14) or (15) described above, including a winding jig configured to wind the line body therearound to form the indicator part.

(17) The present invention further provides the instrument set for inserting a marker for use in a living body according to (16) described above in which the winding jig includes a guide groove configured to define a winding direction of the line body.

(18) The present invention further provides the instrument set for inserting a marker for use in a living body according to (17) described above in which the winding jig includes a plurality of the guide grooves, and the plurality of guide grooves are provided at positions to bend the line body with radii of curvature different from one another, respectively.

Advantageous Effects of Invention

The marker for use in a living body and the instrument set for inserting a marker for use in a living body according to the present invention can provide a beneficial effect that a predetermined site in a living body can be identified easily and accurately.

BRIEF DESCRIPTION OF DRAWINGS

FIG. 1 is a schematic view illustrating an instrument set for inserting a marker for use in a living body according to an embodiment of the present invention.

FIG. 2A is a schematic front view of a marker for use in a living body; FIG. 2B is a schematic bottom view of the marker for use in a living body; and FIG. 2C is a cross-sectional view taken along line A-A in FIG. 2A.

FIG. 4A is a schematic front view of a dispenser; FIG. 4B is a schematic bottom view of the dispenser; and FIG. 4C is a cross-sectional view taken along line C-C in FIG. 4A.

FIGS. 11A and 11B are schematic views showing an example configured to restrict a relative rotation of the marker for use in a living body and a guide part.

DESCRIPTION OF EMBODIMENTS

Figure 3A:
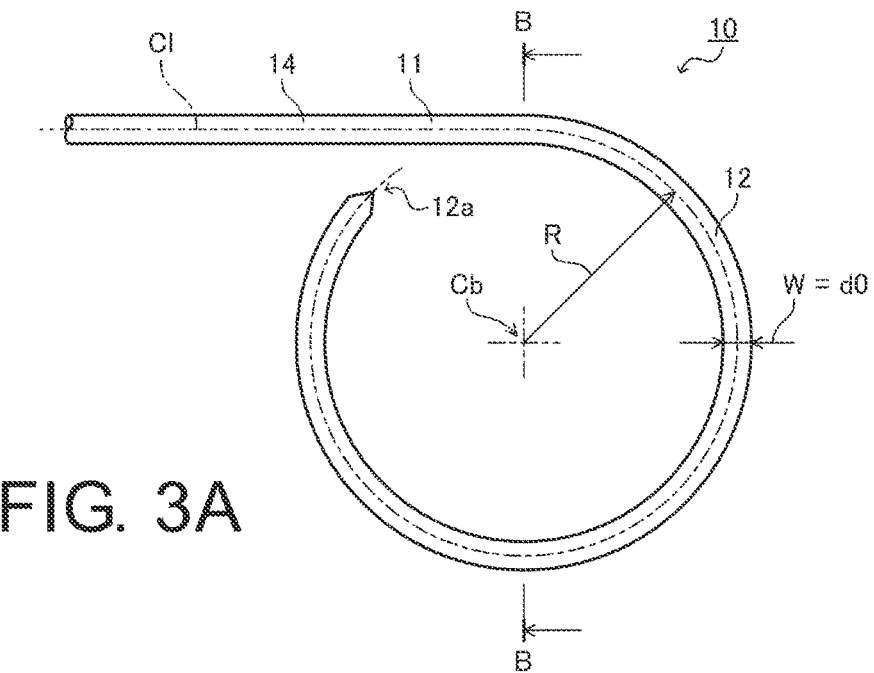
FIG. 3A is a schematic front view illustrating an indicator part in an enlarged manner.

An embodiment of the present invention will be described below with reference to the accompanying drawings. Note that the following figures include omitted or simplified portions for ease of understanding. Note also that shapes or dimensional ratios of elements in the following figures are not necessarily accurate.

FIG. 1 is a schematic view illustrating an instrument set 1 for inserting a marker for use in a living body according to the present embodiment. The instrument set 1 for inserting a marker for use in a living body is used to insert and place a marker (indicator), which has a high visibility in X-ray images, into and at a predetermined site (e.g., a lesion such as cancer tissue) in a living body. As shown in FIG. 1, the instrument set 1 for inserting a marker for use in a living body includes: a marker 10 for use in a living body, at least part of which is placed in a living body; a dispenser 20 configured to insert the marker 10 for use in a living body into a living body; and a winding jig 30 configured to deform the marker 10 for use in a living body into a predetermined shape.

FIG. 2A is a schematic front view of the marker 10 for use in a living body. FIG. 2B is a schematic bottom view of the marker 10 for use in a living body. FIG. 2C is a cross-sectional view taken along line A-A in FIG. 2A. The marker 10 for use in a living body is an indicator that facilitates the identification of cancer tissue and the like by means of X-ray photography in a surgery to remove the cancer tissue and the like. At least part of the marker 10 for use in a living body is placed in a living body. As shown in these figures, the marker 10 for use in a living body is formed by bending a line body 11 having a generally circular cross section with an outer diameter d0 [mm]. The marker 10 for use in a living body includes an indicator part 12, a transporting part 14, and an orientation indicating part 16.

The line body 11 is constituted by a Ti-23Ta-3Sn alloy. Specifically, the line body 11 is constituted by a titanium alloy containing 23 at % of tantalum (Ta) and 3 at % of tin (Sn), relative to the whole taken as 100 atomic percent (at %), with the balance being titanium (Ti) and inevitable impurities.

The Ti-23Ta-3Sn alloy has a high X-ray absorptivity due to the containing of tantalum and tin having relatively large atomic weights, thus providing an excellent contrast property in X-ray photography. In addition, since the Ti-23Ta-3Sn alloy contains no ferromagnetic substances such as iron (Fe), cobalt (Co), and nickel (Ni), this alloy is less likely to be affected by a magnetic field, thus causing no problems such as artifacts or heat generation in MRI. Thus, by making the marker 10 for use in a living body with the line body 11 of the Ti-23Ta-3Sn alloy, the visibility of the marker 10 for use in a living body can be enhanced in an X-ray image and a diagnosis by MRI can be performed with the marker 10 for use in a living body being left in place in a living body.

The Ti-23Ta-3Sn alloy, in particular, has an X-ray absorptivity higher than that of a stainless steel (such as SUS316L, for example), which is a material of a conventional hook wire, and close to that of platinum (Pt) or a platinum-based alloy (such as a platinum-tungsten (Pt—W) alloy or a platinum-gold (Pt—Au) alloy, for example), which has been known as a material of a marker added to catheters, guide wires, or the like. Thus, the Ti-23Ta-3Sn alloy appears in an X-ray image more clearly than the conventional hook wire. While platinum-tungsten alloys have broader utility than platinum alone or platinum-gold alloys in terms of their strength, hardness, or the like, such a platinum-tungsten alloy has a relatively strong magnetic property. Thus, when an MRI machine generates a strong magnetic field, problems such as artifacts or heat generation may occur. The Ti-23Ta-3Sn alloy, on the other hand, has a magnetic property lower than those of platinum-tungsten alloys (for example, an alloy that is obtained by adding 5 to 8 wt % of tungsten to platinum). Thus, the problems are less likely to occur even in a relatively strong magnetic field which causes the problems in platinum-tungsten alloys.

Furthermore, the Ti-23Ta-3Sn alloy has an elastic limit moderately lower than that of a nickel-titanium-based alloy (an alloy containing nickel and titanium as principal components), which is a super-elastic alloy, while having a tensile strength and a Young's modulus comparable to those of the nickel-titanium-based alloy. Thus, by forming the line body 11 from the Ti-23Ta-3Sn alloy, the line body 11 can be plastically deformed appropriately by bending while obtaining strength and flexibility comparable to those of nickel-titanium-based alloys. This can facilitate the forming of the marker 10 for use in a living body.

Figure 3B:
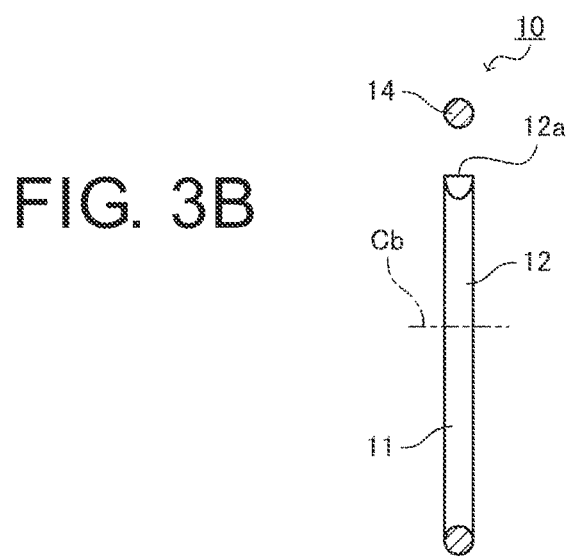
FIG. 3B is a cross-sectional view taken along line B-B in FIG. 3A.

The indicator part 12 is a part to be placed in the vicinity of cancer tissue and the like so as to serve as an indicator. FIG. 3A is a schematic front view illustrating the indicator part 12 in an enlarged manner, and FIG. 3B is a cross-sectional view taken along line B-B in FIG. 3A. The indicator part 12 is configured in a generally C-shape (unclosed circular shape) by bending the line body 11 to have a radius of curvature R. In the present embodiment, such a configuration of the indicator part 12 allows the indicator part 12 to be placed so as to surround cancer tissue and the like. More specifically, the indicator part 12 is configured to be capable of indicating the position of the cancer tissue and the like, and the size of a region (extent) occupied by the cancer tissue and the like, as information on the living body.

The radius of curvature R of the indicator part 12 is set on the basis of a dimension (width) W [mm] of the line body 11 in a direction of the radius of curvature R and an elastic limit (elastic limit strain) ε1 [%] of the line body 11. Specifically, the radius of curvature R of the indicator part 12 is set so as to satisfy the following Expression (1).

$$R > 50 \times W/\varepsilon 1 \qquad (1)$$

Since the line body 11 has a generally circular cross section in the present embodiment, a neutral axis in bending corresponds to a central axis C1 of the line body 11. Therefore, the radius of curvature R corresponds to a distance from a center of curvature Cb to the central axis C1 of the line body 11. The width W has the same value as the outer diameter d0. In the present embodiment, the elastic limit ε1 is defined as elongation when 0.5% strain (permanent strain) remains after unloading in a tensile test.

By setting the radius of curvature R as described above, the indicator part 12 can be deformed into a generally linear shape within a range of elastic deformation. More specifically, when the portion that has been bent with the radius of curvature R is deformed into a linear shape, a maximum strain εm [%] on an expanded side and a contracted side is calculated as εm=±100×{πR−π(R−W/2)}/πR=±50×W/R. Thus, the maximum strain εm can be set so as not to exceed the elastic limit ε1 by setting the radius of curvature R as in Expression (1).

In the present embodiment, by configuring the indicator part 12 in a shape satisfying Expression (1), the indicator part 12 can be inserted into a living body while temporarily being deformed into a generally linear shape and then can be returned to its original shape by the restoring force of elastic deformation. This can reduce a degree of invasiveness to a living body when the indicator part 12 is inserted into the living body.

While the size of the indicator part 12 is not limited to any particular size, the indicator part 12 preferably has a size capable of surrounding a circular region having a diameter in a range of not smaller than 3 mm and not larger than 10 mm in order to surround the periphery of cancer tissue and the like, as appropriate. Moreover, the outer diameter d0 of the line body 11 that forms the indicator part 12 is not limited to any particular value. Too large outer diameter, however, results in a high degree of invasiveness to a living body, whereas too small outer diameter results in deteriorated visibility in an X-ray image. Therefore, from the viewpoint of balancing the degree of invasiveness to the living body and the visibility, the outer diameter d0 of the line body 11 preferably falls within a range of not smaller than 0.1 mm and not larger than 0.3 mm.

While the elastic limit ε1 of the line body 11 is not limited to any particular value, the elastic limit ε1 preferably falls within a range of not lower than 2% and not higher than 6%. When the elastic limit ε1 of the line body 11 is lower than 2%, a possibility that the indicator part 12 is plastically deformed accidentally in a living body increases and the radius of curvature R in which the indicator part 12 can be deformed into a linear shape within a range of elastic deformation increases. When the elastic limit ε1 of the line body 11 is higher than 6%, it becomes difficult to bend and plastically deform the line body 11 with fingers when the indicator part 12 is formed.

In the present embodiment, the line body 11 is constituted by the Ti-23Ta-3Sn alloy as described above. Thus, by being subjected to an appropriate heat treatment after a cold wire drawing process, the line body 11 can obtain a tensile strength and a Young's modulus comparable to those of nickel-titanium-based alloys and the elastic limit ε1 in a range of not lower than 2% and not higher than 6%.

Note that the material of the line body 11 is not limited to the Ti-23Ta-3Sn alloy. For example, a Ti-19Ta-4.5Sn alloy, a Ti-23Ta-1.5Sn alloy, a Ti-23Ta-4.5Sn alloy, a Ti-27Ta-1.5Sn alloy, a Ti-27Ta-3Sn alloy, a Ti-27Ta-4.5Sn alloy, and the like may be used. Because of the inclusion of an appropriate amount of tantalum or tantalum and tin, an X-ray absorptivity higher than those of stainless steels as well as a magnetic property lower than those of platinum-tungsten alloys can be obtained. The use of a titanium alloy containing 15 to 27 at % of tantalum (Ta) and 0 to 8 at % of tin (Sn), relative to the whole taken as 100 atomic percent (at %), with the balance being titanium (Ti) and inevitable impurities can yield a tensile strength and a Young's modulus comparable to those of nickel-titanium-based alloys as well as a preferred elastic limit ε1.

Furthermore, a titanium alloy containing an element other than tantalum and tin may be used as a material of the line body 11. Any titanium alloy is easy to obtain preferred mechanical properties (such as a tensile strength, a Young's modulus, and an elastic limit). Furthermore, any titanium alloy having an X-ray absorptivity higher than those of stainless steels and having a magnetic property lower than those of platinum-tungsten alloys, which have been obtained by the inclusion of an appropriate added element(s), can obtain preferred characteristics as a marker for indicating information on a living body, i.e., a high contrast property in X-ray photography and a lower possibility of causing problems in a diagnosis by MRI.

When the indicator part 12 has a high contrast property in X-ray photography, cancer tissue and the like can be identified with relatively low X-ray intensity. Thus, the X-ray dose the living body receives can be reduced. Furthermore, the usage of a contrast medium can be reduced, thereby making it possible to reduce the physical burden. In addition, if the indicator part 12 is less likely to cause problems in a diagnosis by MRI, the diagnosis method after the placement of the marker 10 for use in a living body is no longer limited to any particular method. This can increase a range of application of the marker 10 for use in a living body. In addition, a medium- to long-term follow-up can be done more easily with the marker 10 for use in a living body being left in place.

A tip of the indicator part 12 has a blade 12a formed to facilitate the insertion of the indicator part 12 into body tissue. In the present embodiment, the blade 12a is configured to be generally parallel to a direction of the center of curvature Cb (the horizontal direction in FIG. 3B). This allows the indicator part 12 to be inserted into the body tissue while being smoothly returned from the linear shape to the circular shape.

Referring back to FIG. 2, the transporting part 14 is a part to be held by an operator, such as a doctor, in order to push the indicator part 12 into a living body. The transporting part 14 is constituted by the line body 11 having a generally linear shape, which is continuous with the indicator part 12. A length L1 of the transporting part 14 is set to a value appropriate for the insertion depth of the indicator part 12. The orientation indicating part 16 is a part for indicating the orientation of the indicator part 12 relative to the transporting part 14. The orientation indicating part 16 is provided in one side of the transporting part 14 opposite to the indicator part 12. The orientation indicating part 16 is formed by bending the line body 11 generally at a right angle in the same direction as the bending direction of the indicator part 12 (the downward direction in FIG. 2A).

FIG. 4A is a schematic front view of the dispenser 20. FIG. 4B is a schematic bottom view of the dispenser 20. FIG. 4C is a cross-sectional view taken along line C-C in FIG. 4A. The dispenser 20 is inserted into a living body, with the marker 10 for use in a living body passing therethrough, in order to insert the marker 10 for use in a living body into the living body and guide the indicator part 12 to a desired location. As shown in these figures, the dispenser 20 includes a tubular guide part 22, and a base part 24 to which the guide part 22 is joined. The dispenser 20 has a structure similar to an injection needle.

The guide part 22 is a part configured to house the indicator part 12 of the marker 10 for use in a living body so that the indicator part 12 can be moved in an axial direction (the horizontal direction in FIGS. 4A and 4B) while being deformed into a generally linear shape. The guide part 22 is also a part to be inserted into a living body with the indicator part 12 and part of the transporting part 14 being housed therein. The guide part 22 is a generally cylindrical member having an inner diameter d1 and an outer diameter d2. The guide part 22 has a tip shape similar to that of a needle shaft of an injection needle. The inner diameter d1 of the guide part 22 is set to a value slightly larger than the outer diameter d0 of the line body 11 so as to deform the housed indicator part 12 into a generally linear shape and to move the indicator part 12 and the transporting part 14 smoothly in the axial direction. The outer diameter d2 of the guide part 22 is set to a value that gives appropriate strength and stiffness to the guide part 22. A length L2 of the guide part 22 is set to a value appropriate for the insertion depth of the indicator part 12.

The tip of the guide part 22 is provided with a contrast enhancement part 22a coated with a metal having a high X-ray absorptivity such as gold (Au) or platinum (Pt). The tip of the guide part 22 is configured so that the position thereof can be easily checked by X-ray photography during the insertion of the guide part 22. Note that the contrast enhancement part 22a may be configured to enhance a contrast property in ultrasonic diagnostic equipment.

The base part 24 is a part to be held by an operator when the guide part 22 is inserted. The base part 24 is constituted by an appropriate resin. The base part 24 is configured to have a diameter larger than that of the guide part 22 in order to facilitate the holding and pushing during the insertion. The base part 24 is also provided with a communication hole 24a communicated with the interior of the guide part 22. The orientation indicating part 16 and part of the transporting part 14 in the marker 10 for use in a living body project toward the hand side of an operator through the communication hole 24a. That is, the dispenser 20 is configured so that an operator can operate the marker 10 for use in a living body by means of the transporting part 14 and the orientation indicating part 16 projecting from the communication hole 24a and can check the orientation of the indicator part 12.

Note that an existing injection needle may be used as the dispenser 20. When the outer diameter d0 of the line body 11 that forms the marker 10 for use in a living body is 0.2 mm, for example, a 27G injection needle can be used as the dispenser 20. When the outer diameter d0 is 0.3 mm, a 25G injection needle can be used as the dispenser 20.

Figure 5A:
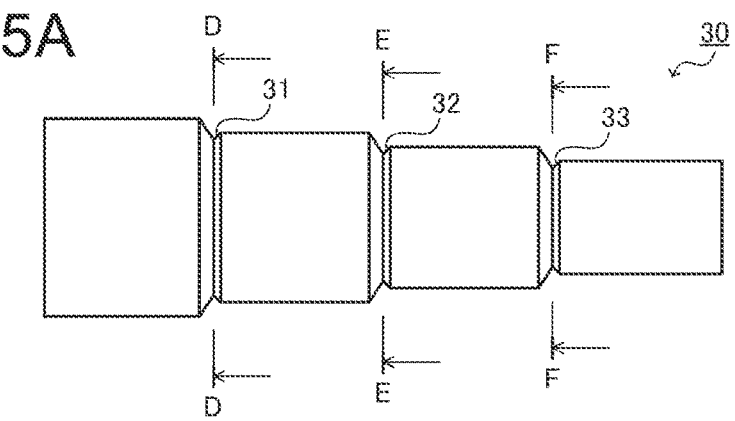
FIG. 5A is a schematic front view of a winding jig.
Figure 5B:
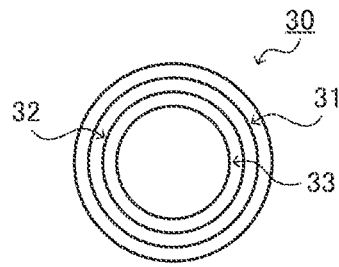
FIG. 5B is a right side view of the winding jig.
Figure 5C:
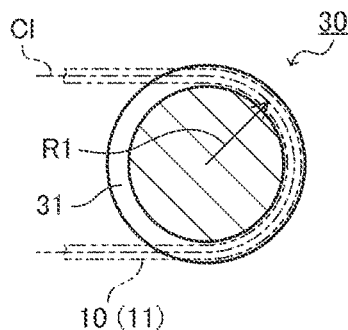
FIG. 5C is a cross-sectional view taken along line D-D in FIG. 5A.
Figure 5D:
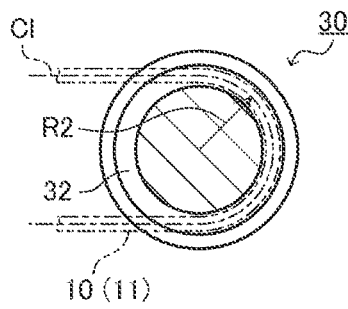
FIG. 5D is a cross-sectional view taken along line E-E in FIG. 5A.
Figure 5E:
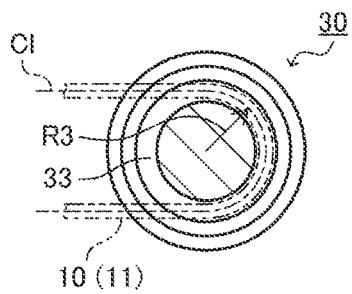
FIG. 5E is a cross-sectional view taken along line F-F in FIG. 5A.

FIG. 5A is a schematic front view of the winding jig 30, and FIG. 5B is a right side view of the winding jig 30. FIG. 5C is a cross-sectional view taken along line D-D in FIG. 5A. FIG. 5D is a cross-sectional view taken along line E-E in FIG. 5A. FIG. 5E is a cross-sectional view taken along line F-F in FIG. 5A. The winding jig 30 is used to achieve plastic deformation by winding and bending the line body 11 with a predetermined outer diameter d0 therearound in order to form the indicator part 12 with a predetermined radius of curvature R. As shown in these figures, the winding jig 30 is configured in a stepped columnar shape having four different outer diameters. At three stepped portions, guide grooves 31, 32, and 33 in order of decreasing outer diameter are formed along their circumferential directions.

The guide grooves 31 to 33 are configured to guide the wound line body 11 and define the winding direction. As shown in FIG. 5C, the guide groove 31 is configured so that winding the line body 11 along the guide groove 31 causes the line body 11 having the predetermined outer diameter d0 to bend with a radius of curvature R1. As shown in FIG. 5D, the guide groove 32 is configured to bend the line body 11 having the predetermined outer diameter d0 with a radius of curvature R2 smaller than the radius of curvature R1. As shown in FIG. 5E, the guide groove 33 is configured to bend the line body 11 having the predetermined outer diameter d0 with a radius of curvature R3 smaller than the radius of curvature R2.

In the present embodiment, the three guide grooves 31 to 33 are provided. Winding the line body 11 around the guide groove 31, the guide groove 32, and the guide groove 33 in this order increases the magnitude of strain imparted to the line body 11 in stages. This allows the line body 11 to be plastically deformed appropriately, thereby making it possible to form the indicator part 12 having the predetermined radius of curvature R in a stable manner.

The line body 11 after being wound along the guide grooves 31 to 33 is in a state being bent with radii of curvature larger than the radii of curvature R1 to R3 at the time of winding, respectively, by a predetermined ratio due to spring back. Therefore, the radius of curvature R3 in the guide groove 33 is set to a value smaller than the finally-achieved radius of curvature R of the indicator part 12 by the predetermined ratio.

Even when the line body 11 is bent with the same radii of curvature R1 to R3, the magnitude of strain imparted to the line body 11 varies depending on the outer diameter d0. Therefore, the finally-achieved radius of curvature R also varies depending on the outer diameter d0. Accordingly, the radii of curvature R1 to R3 in the guide grooves 31 to 33 are set to different values for different outer diameters d0 of the line body 11 even when the same radius of curvature R is finally achieved. Moreover, the winding jig 30 preferably indicates values of an applicable outer diameter d0 of the line body 11 and a finally-achieved radius of curvature R.

As described above, the line body 11 is constituted by the Ti-23Ta-3Sn alloy in the present embodiment. This allows for the easy formation of the indicator part 12 having the predetermined radius of curvature R simply by pressing, and holding, a tip of the line body 11 against the guide grooves 31 to 33 with a nail of one hand, for example, and then pinching the line body 11 with fingers of the other hand and winding the line body 11 along the guide grooves 31 to 33. In the present embodiment, in particular, the guide grooves 31 to 33 are provided in the stepped portions. This allows the line body 11 to be easily seized and to be easily set along the guide grooves 31 to 33. Moreover, by preparing different types of winding jigs 30 having different finally-achieved radii of curvature R, a doctor and the like can form the indicator part 12 having a needed size with one's own hand after checking the size of cancer tissue and the like in an X-ray image and the like.

Note that the winding jig 30 may be provided with a holding mechanism appropriately configured to hold the tip of the line body 11. Moreover, the number of bending the line body 11 in stages is not limited to three but may be other numbers. It is obvious that the indicator part 12 may be formed not by bending the line body 11 in stages but by a single wind.

A method of using the instrument set 1 for inserting a marker for use in a living body will be described next.

Figure 6A:
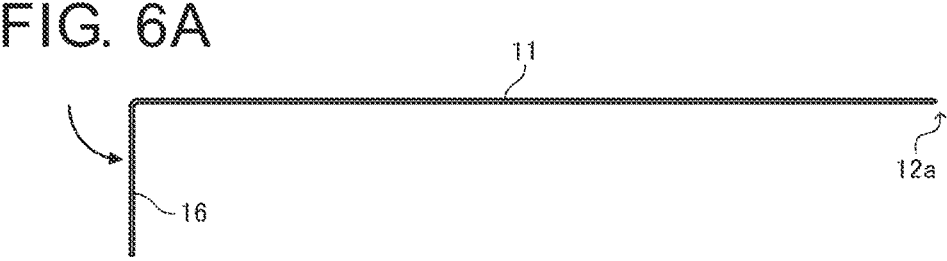
FIGS. 6A to 6E are schematic views illustrating a method of placing the marker for use in a living body by the instrument set for inserting a marker for use in a living body.

FIGS. 6A to 6E and FIGS. 7A to 7E are schematic views illustrating a method of placing the marker 10 for use in a living body by the instrument set 1 for inserting a marker for use in a living body. In the placement of the marker 10 for use in a living body, the hand side (the opposite side to the tip provided with the blade 12a) of the line body 11 having a linear shape is first bent generally at a right angle to form the orientation indicating part 16 as shown in FIG. 6A.

Figure 6B:
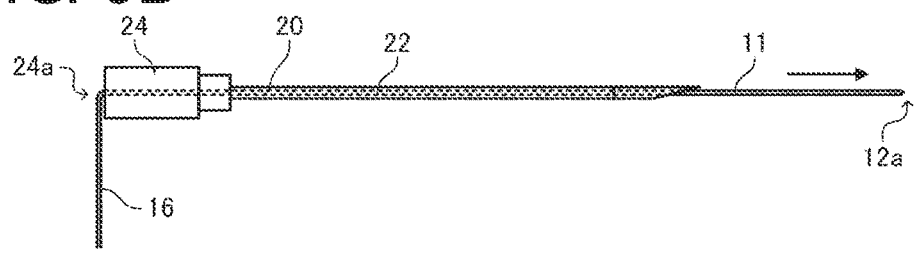
Figure 6C:
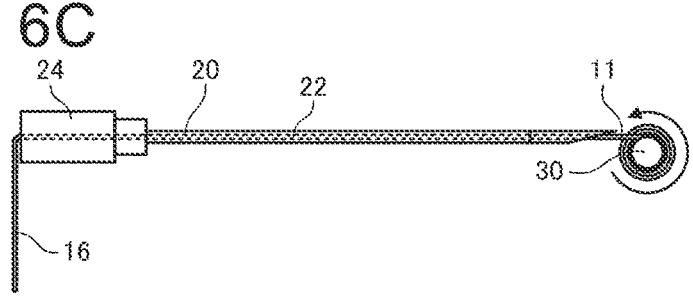
Figure 6D:
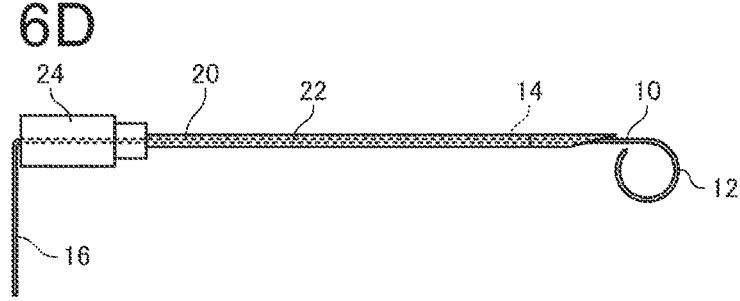

Subsequently, the line body 11 is passed through the dispenser 20 from the communication hole 24a of the base part 24 so that a tip portion thereof projects from the guide part 22 as shown in FIG. 6B. The portion of the line body 11 projecting from the guide part 22 is then wound around the winding jig 30 to form the indicator part 12 having a predetermined size as shown in FIG. 6C. In this manner, the marker 10 for use in a living body is formed as shown in FIG. 6D.

Figure 6E:
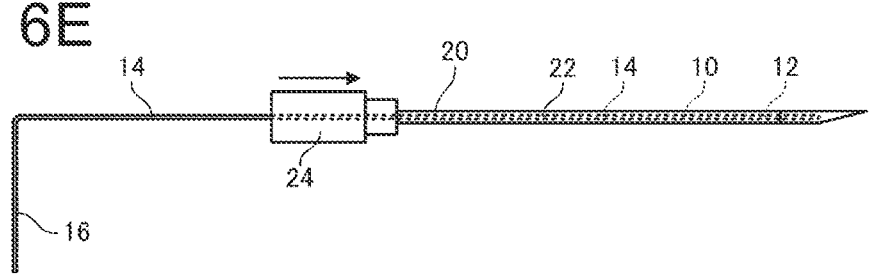

Once the marker 10 for use in a living body is appropriately formed, the dispenser 20 is moved toward the indicator part 12 so as to elastically deform the indicator part 12 into a generally linear shape and house the indicator part 12 in the guide part 22 as shown in FIG. 6E. In this manner, the dispenser 20 is ready to be inserted together with the marker 10 for use in a living body.

Note that the indicator part 12 may be formed first in the line body 11 and the orientation indicating part 16 may be formed after the line body 11 is passed through the dispenser 20. In this case, the line body 11 having the indicator part 12 may be subjected to an appropriate heat treatment to stabilize the shape of the indicator part 12.

Figure 7A:
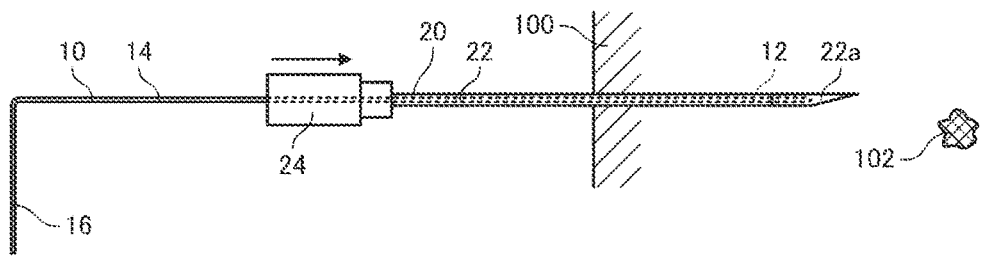
FIGS. 7A to 7E are schematic views illustrating the method of placing the marker for use in a living body by the instrument set for inserting a marker for use in a living body.
Figure 7B:
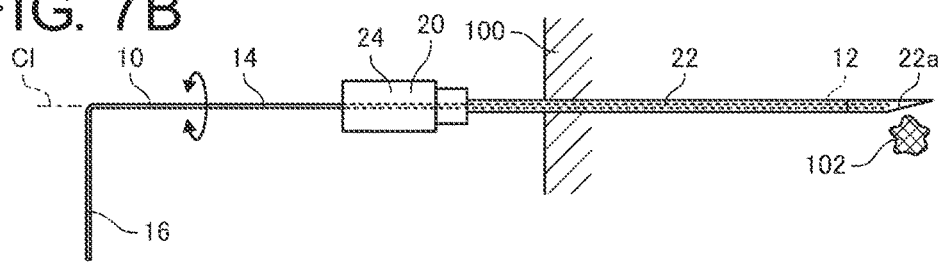

Subsequently, while checking the position of the contrast enhancement part 22a in an X-ray image, the guide part 22 is inserted, together with the marker 10 for use in a living body, toward a target site 102, such as cancer tissue, in a living body 100 until the tip of the guide part 22 reaches the vicinity of the target site 102 as shown in FIG. 7A. Once the tip of the guide part 22 reaches the vicinity of the target site 102, the transporting part 14 is rotated about the central axis C1 to adjust the orientation of the indicator part 12 relative to the target site 102 as shown in FIG. 7B. When the orientation of the guide part 22 needs to be adjusted, the dispenser 20 is rotated about the central axis C1 of the transporting part 14.

Figure 7C:
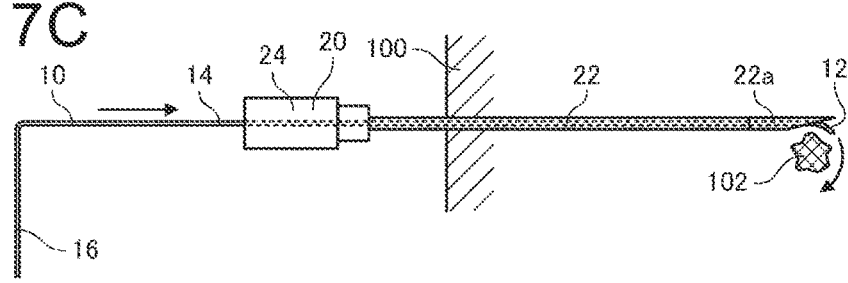

Once the orientation of the indicator part 12 is appropriately adjusted, the transporting part 14 of the marker 10 for use in a living body is pushed in so that the indicator part 12 projects from the tip of the guide part 22 as shown in FIG. 7C. This causes the indicator part 12 to be inserted into the living body 100 so as to surround the target site 102 while being returned to the circular shape.

Figure 7D:
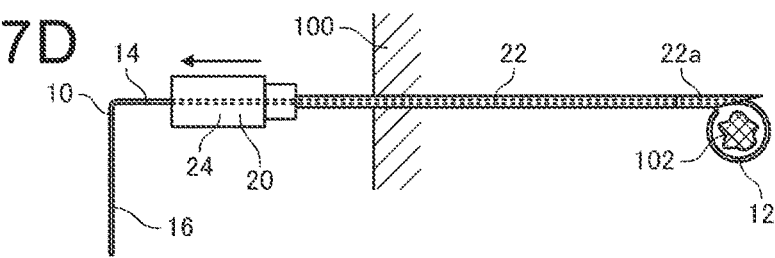
Figure 7E:
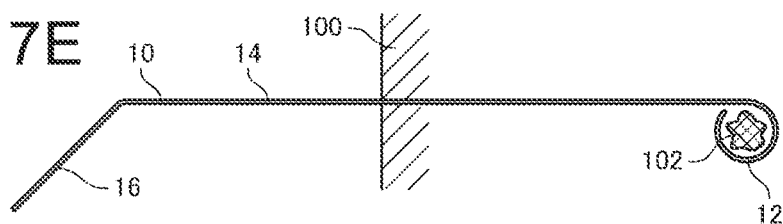

Once the entire indicator part 12 projects from the guide part 22 and appropriately surrounds the target site 102, the dispenser 20 is withdrawn from the living body 100 as shown in FIG. 7D to leave only the marker 10 for use in a living body in place in the living body 100 as shown in FIG. 7E. In this manner, the placement of the marker 10 for use in a living body is completed. Note that part of the transporting part 14 and the orientation indicating part 16 in the marker 10 for use in a living body are exposed to the outside of the living body 100. Moreover, the orientation indicating part 16 is plastically deformed by being passed through the guide part 22 during the withdrawal of the dispenser 20, thus resulting in a change in bend angle.

Figure 8A:
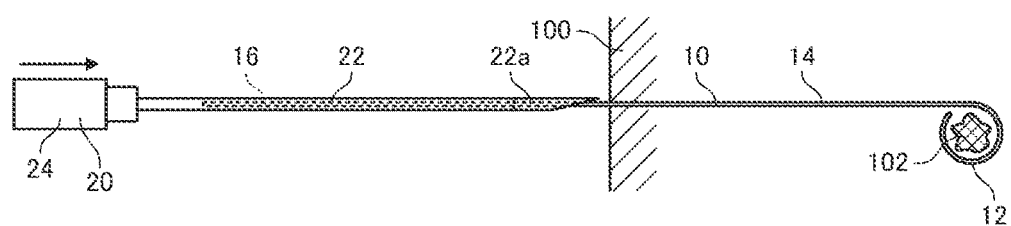
FIGS. 8A to 8C are schematic views illustrating a method of removing the marker for use in a living body by the instrument set for inserting a marker for use in a living body.
Figure 8B:
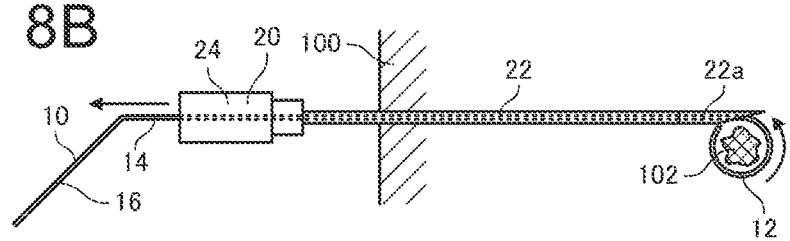
Figure 8C:
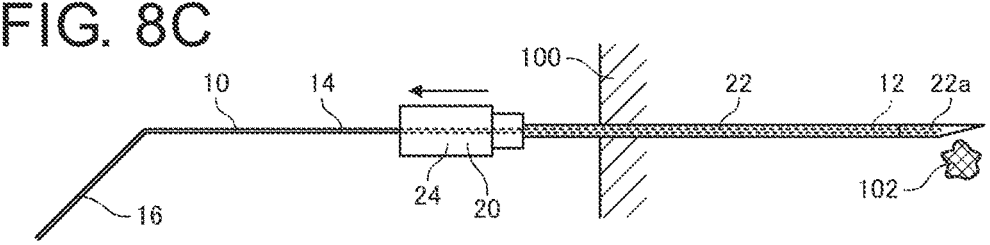

FIGS. 8A to 8C are schematic views illustrating a method of removing the marker 10 for use in a living body by the instrument set 1 for inserting a marker for use in a living body. In the removal of the marker 10 for use in a living body, the orientation indicating part 16 and the transporting part 14 of the marker 10 for use in a living body that are exposed to the outside of the living body 100 are first inserted into the guide part 22 of the dispenser 20 as shown in FIG. 8A. Thereafter, while checking the position of the contrast enhancement part 22a in an X-ray image, the guide part 22 is inserted into the living body 100 along the transporting part 14 until the tip of the guide part 22 reaches the vicinity of the indicator part 12.

Once the tip of the guide part 22 reaches the vicinity of the indicator part 12, the transporting part 14 is pulled toward the hand side so that the indicator part 12 is housed in the guide part 22 while being elastically deformed into a generally linear shape as shown in FIG. 8B. Once the indicator part 12 is housed in the guide part 22, the dispenser 20 is withdrawn together with the marker 10 for use in a living body as shown in FIG. 8C. In this manner, the removal of the marker 10 for use in a living body is completed.

Other configurations of the instrument set 1 for inserting a marker for use in a living body will be described next.

Figure 9A:
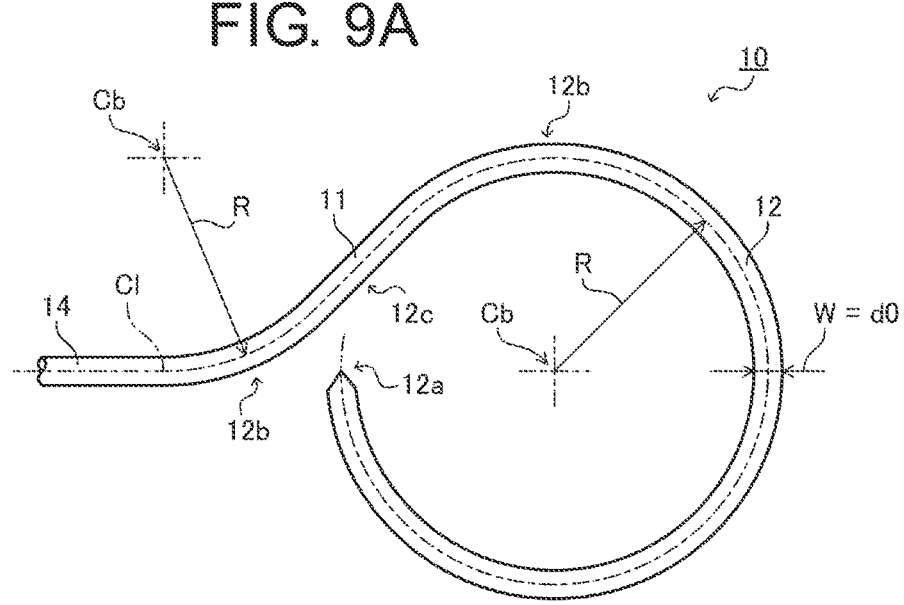
FIGS. 9A and 9B are schematic views illustrating another configuration example of the indicator part.
Figure 9B:
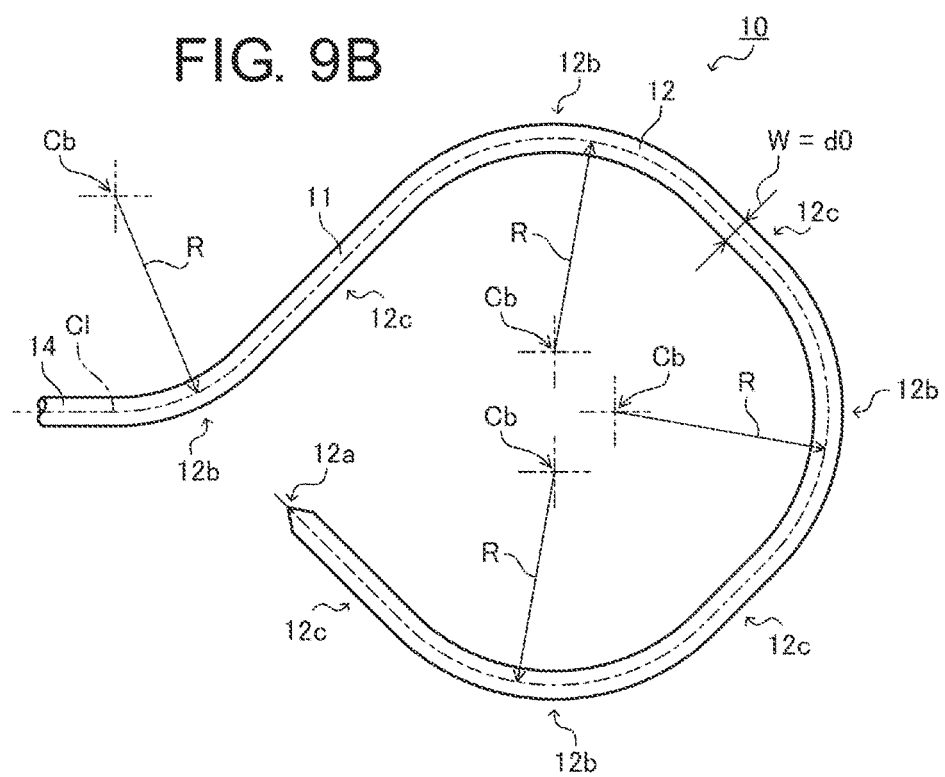

FIGS. 9A and 9B are schematic views illustrating another configuration example of the indicator part 12. According to the example shown in these figures, the indicator part 12 is provided with a plurality of bent portions 12b, and a linear portion 12c connects between two of the bent portions 12b. Also in this case, the indicator part 12 can be deformed into a generally linear shape within a range of elastic deformation by setting the radius of curvature R of each bent portion 12b so as to satisfy the above-described Expression (1). The shape of the indicator part 12 is not limited to any particular shape. Combining the plurality of bent portions 12b with the linear portion(s) 12c as just described can provide various shapes of the indicator part 12.

For example, by placing the indicator part 12 having a different shape depending on a type or state of the target site 102 such as cancer tissue, not only the position and extent of the cancer tissue and the like, but also the type or state of the cancer tissue and the like can be indicated as information on the living body. Moreover, the indicator part 12 may have a different shape depending on, for example, the date when the marker 10 for use in a living body is placed or a material of the marker 10 for use in a living body so as to indicate information on the marker 10 for use in a living body (the indicator part 12) as well as the information on the living body. More specifically, such different shapes of the indicator part 12 can provide different images of the indicator part 12 shown in X-ray images, and such differences in the X-ray image of the indicator part 12 can indicate a wide variety of information.

In the example shown in FIGS. 9A and 9B, the centers of curvature Cb of the bent portions 12b are all parallel to one another, so that the indicator part 12 has a two-dimensional shape. The centers of curvature Cb of the bent portions 12b, however, may intersect with one another as appropriate so that the indicator part 12 has a three-dimensional shape. Alternatively, the bent portion 12b may be bent helically or spirally. It is obvious that the linear portion 12c may not be provided between the two bent portions 12b, but the two bent portions 12b may be directly connected to each other. Furthermore, the indicator part 12 may have a shape not to surround the target site 102. In this case, the indicator part 12 may have a shape of a character, a number, or a symbol, for example, so that a variety of information can be indicated more clearly or more information can be indicated.

Figure 10A:
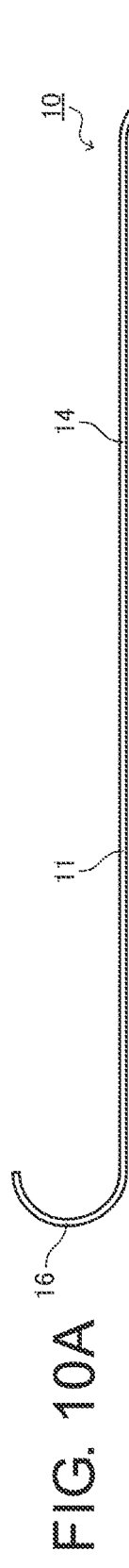
FIGS. 10A to 10D are schematic views illustrating other configuration examples of an orientation indicating part.
Figure 10B:
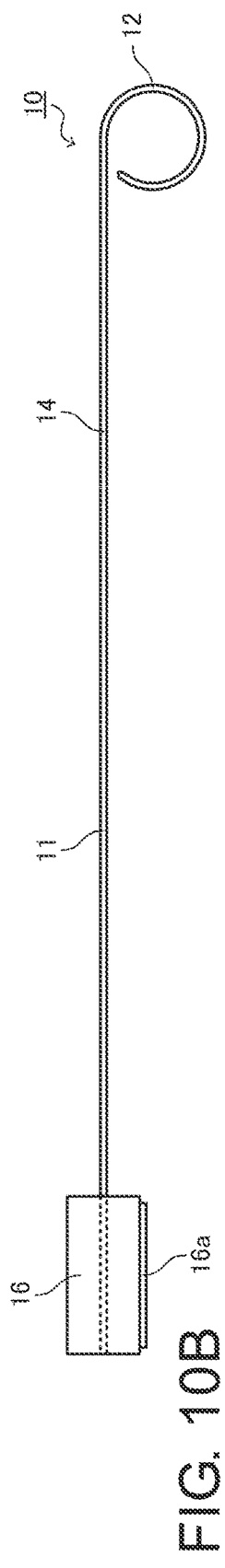
Figure 10C:
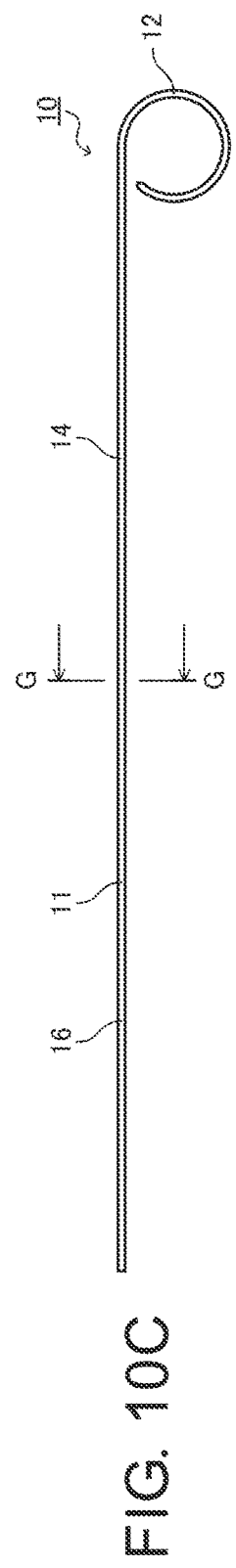
Figure 10D:

FIGS. 10A to 10D are schematic views illustrating other configuration examples of the orientation indicating part 16. FIG. 10D is a cross-sectional view taken along line G-G in FIG. 10C. The shape of the orientation indicating part 16, which is formed by bending the line body 11, is not limited to any particular shape. The orientation indicating part 16 may be configured to have various shapes such as an arc shape as shown in FIG. 10A, for example. Moreover, the orientation indicating part 16 is not limited to those obtained by bending the line body 11 but may be formed by other members. In the example shown in FIG. 10B, the orientation indicating part 16 is constituted by a generally cylindrical member connected to the transporting part 14 and a protrusion 16a provided on an outer circumferential surface of the orientation indicating part 16 indicates the orientation of the indicator part 12. The provision of a member having a diameter larger than that of the line body 11 in the transporting part 14 as just described can improve the operability of the transporting part 14.

FIGS. 10C and 10D show an example in which the line body 11 has an elliptical cross-sectional shape and the orientation indicating part 16 is constituted by this cross-sectional shape. As just described, the line body 11 may have a cross-sectional shape having a longitudinal direction such as an ellipse, an oval, or a rectangle, and the longitudinal direction of the cross-sectional shape may indicate the orientation of the indicator part 12. In this case, note that the entire marker 10 for use in a living body may have a cross-sectional shape having a longitudinal direction or part of the marker 10 for use in a living body, such as the hand side of the transporting part 14, may have a cross-sectional shape having a longitudinal direction.

FIGS. 11A and 11B are schematic views showing an example configured to restrict a relative rotation of the marker 10 for use in a living body and the guide part 22. FIG. 11B is a cross-sectional view taken along line H-H in FIG. 11A. In this example, the line body 11 and the guide part 22 are configured to have elliptical cross-sectional shapes so as to restrict a relative rotation of the marker 10 for use in a living body and the guide part 22 about the axial direction of the guide part 22. In this manner, the orientation of the indicator part 12 relative to the dispenser 20 can be prevented from changing, and the transporting part 14 or the indicator part 12 in the guide part 22 can be prevented from twisting. This can facilitate the operations of the marker 10 for use in a living body and the dispenser 20.

Note that the cross-sectional shapes of the line body 11 and the guide part 22 in this case are not limited to an ellipse. The relative rotation may be restricted by other cross-sectional shapes such as polygonal shapes. Alternatively, the relative rotation may be restricted by modifying the cross-sectional shapes partially.

Figure 12A:
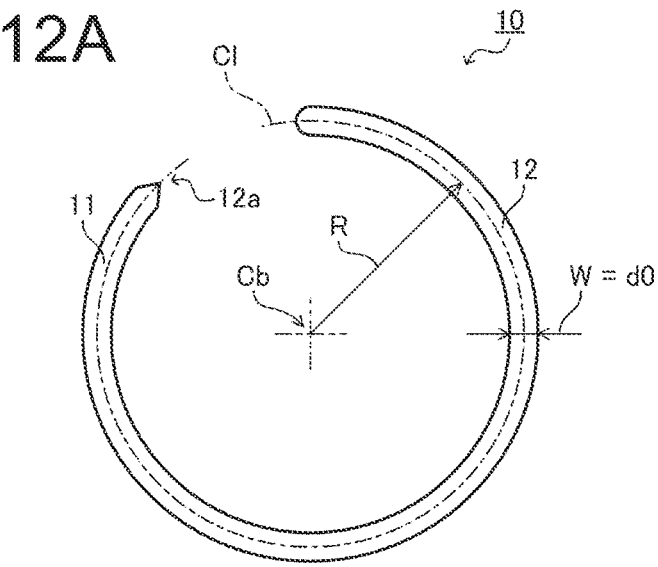
FIGS. 12A to 12C are schematic views showing an example in which the marker for use in a living body is configured to have the indicator part only.
Figure 12B:
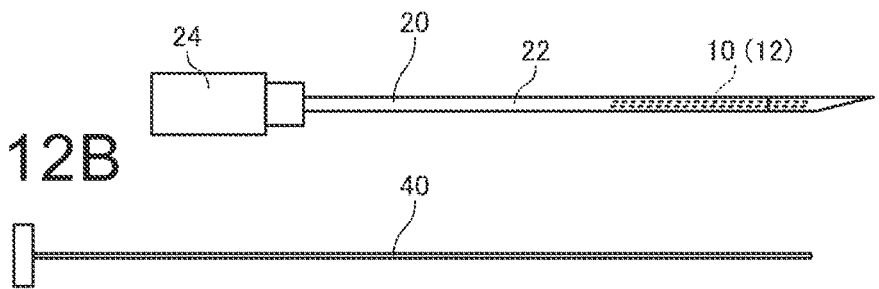
Figure 12C:
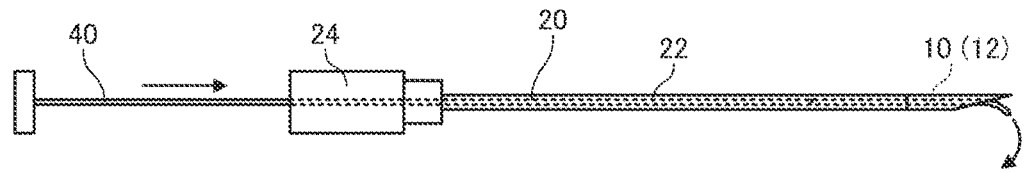

FIGS. 12A to 12C are schematic views showing an example in which the marker 10 for use in a living body is configured to have the indicator part 12 only. The marker 10 for use in a living body may be configured to have the indicator part 12 only as shown in FIG. 12A in an enlarged manner without being limited to those including the transporting part 14 and the orientation indicating part 16. In this case, a generally rod-shaped pusher 40 capable of being passed through the guide part 22 of the dispenser 20 may be prepared, and the pusher 40 may be used to push the marker 10 for use in a living body that has been deformed into a generally linear shape and housed in the guide part 22 out of the guide part 22 as shown in FIGS. 12B and 12C, for example.

Note that the indicator part 12 in this case may be formed by winding the line body 11 around the winding jig 30 and then cutting the line body 11 in an appropriate length or by other known methods. Although the illustration is omitted, it is obvious that the indicator part 12 can take various shapes in this case too.

When the marker 10 for use in a living body is configured to have the indicator part 12 only, the orientation of the indicator part 12 in the living body 100 can be adjusted by restricting the relative rotation of the marker 10 for use in a living body and the guide part 22 about the axial direction of the guide part 22. More specifically, rotating the dispenser 20 about the axial direction of the guide part 22 causes the marker 10 for use in a living body housed in the dispenser 20 to rotate together, thus making it possible to adjust the orientation of the indicator part 12. Furthermore, the dispenser 20 may be provided with an appropriate orientation indicating part.

Figure 13A:
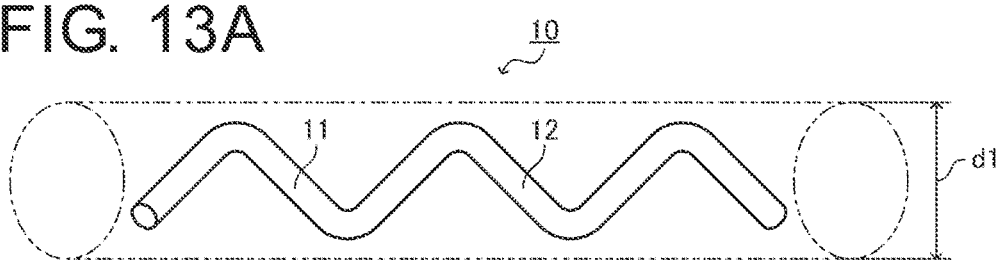
FIGS. 13A to 13C are schematic perspective views illustrating examples in each of which the marker for use in a living body is configured so that the indicator part can be housed in the guide part without being deformed.
Figure 13B:
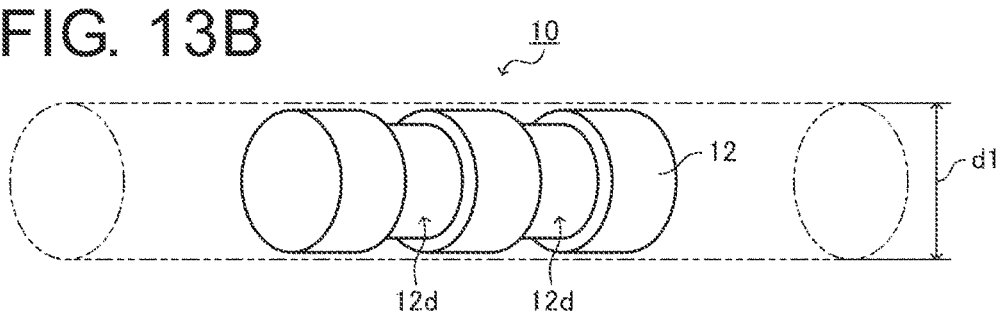
Figure 13C:
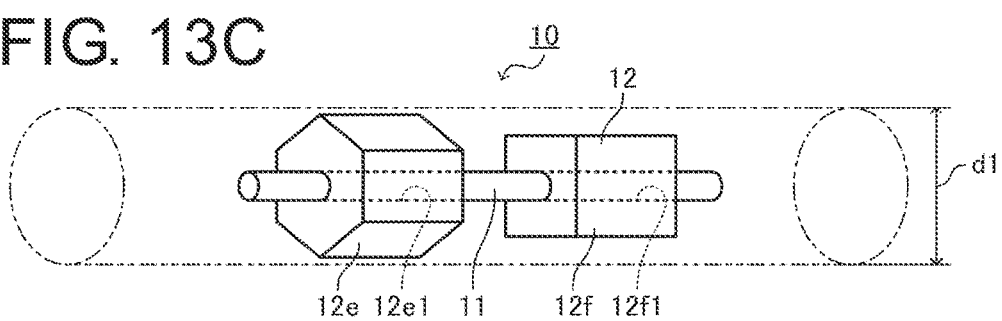

FIGS. 13A to 13C are schematic perspective views illustrating examples in each of which the marker 10 for use in a living body is configured so that the indicator part 12 can be housed in the guide part 22 without being deformed. When the marker 10 for use in a living body can be configured in a relatively compact manner, or when the inner diameter d1 of the guide part 22 in the dispenser 20 can be configured to have a relatively large diameter, the indicator part 12 may be housed in the guide part 22 without being deformed.

FIG. 13A shows an example in which the indicator part 12 is formed by bending the relatively thin line body 11 in a zig-zag manner. As just described, the indicator part 12 may be housed in the guide part 22 while keeping such a bent state. FIG. 13B shows an example in which the indicator part 12 is formed by a member having a stepped columnar shape, which is formed by machining or casting, for example. As just described, the indicator part 12 may be formed by a method other than bending the line body 11. In such a case, since the number of variations in the shape of the indicator part 12 can be increased, the types of information indicated by an X-ray image of the indicator part 12 can be increased. The indicator part 12 can be visually recognized by ultrasonic diagnostic equipment by providing an appropriate recess 12d on a surface of the indicator part 12 to adjust ultrasonic reflection characteristics.

FIG. 13C shows an example in which the indicator part 12 is formed by combining a plurality of members together. Specifically, the indicator part 12 in this example includes: a first member 12e having a generally hexagonal prism shape; a second member 12f having a generally quadrangular prism shape; and the line body 11 passed through insertion holes 12e1 and 12f1 provided in the first and second members 12e and 12f. The number of variations in the shape of the indicator part 12 can be further increased by combining a plurality of members to form the indicator part 12 as just described.

The embodiment of combining a plurality of members together is not limited to that shown in FIG. 13C. Various combinations can be employed such that columnar members are directly engaged with each other, or the line body 11 is wound around the outer periphery of a columnar member, for example. Moreover, an X-ray image of the indicator part 12 can be adjusted by appropriately combining members each having a different X-ray absorptivity.

The examples shown in FIGS. 13A to 13C show cases where the marker 10 for use in a living body is configured to have the indicator part 12 only. However, it is obvious that the transporting part 14 and the orientation indicating part 16 may be provided. Although the illustration is omitted, the indicator part 12 may be constituted by combining a portion having a shape not to be deformed when housed in the guide part 22 with a portion having a shape to be deformed when housed in the guide part 22. For example, part of the generally C-shaped indicator part 12 shown in FIG. 12A may be formed in a zig-zag manner, or a surface of the indicator part 12 may have irregularities. Alternatively, the generally C-shaped indicator part 12 may be combined with another member.

Besides the above, although the illustration is omitted, the instrument set 1 for inserting a marker for use in a living body may include no winding jig 30. In other words, the indicator part 12 may be formed by an appropriate known method other than the winding to the winding jig 30. The indicator part 12 may be formed by means of hot working. The instrument set 1 for inserting a marker for use in a living body may include a plurality of markers 10 for use in a living body in which the indicator parts 12 having sizes or shapes different from one another have been formed in advance. Furthermore, the plurality of markers 10 for use in a living body in this case may be set in individual dispensers 20 in advance.

As described above, the marker 10 for use in a living body according to the present embodiment includes the indicator part 12 to be placed in the living body 100 for a predetermined period of time, and the indicator part 12 is configured to indicate information on the living body 100 or information on the indicator part 12 by means of differences in X-ray image. Such a configuration allows for indicating a variety of information together with the position of the target site 102, such as cancer tissue, simply by taking X-ray photography. Thus, the predetermined site in the living body can be identified easily and accurately.

At least a part of the indicator part 12 is constituted by a titanium alloy that has an X-ray absorptivity higher than those of stainless steels and a magnetic property lower than those of platinum-tungsten alloys. This can yield preferred mechanical properties and preferred characteristics as a marker for indicating information on a living body, i.e., a high contrast property in X-ray photography and a lower possibility of causing problems in a diagnosis by MRI.

Such a titanium alloy constituting the indicator part 12 preferably has an elastic limit εl of not lower than 2% and not higher than 6%. Setting the elastic limit to 2% or higher prevents the indicator part 12 from being plastically deformed accidentally in the living body 100 and allows for the formation of the indicator part 12 having an appropriate size. Moreover, setting the elastic limit to 6% or lower allows the line body 11 to be bent relatively easily with fingers to form the indicator part 12.

A titanium alloy constituting the indicator part 12 preferably contains tantalum or contains tantalum and tin. This can yield preferred mechanical properties as well as an X-ray absorptivity close to that of platinum (Pt) or a platinum-based alloy (such as a platinum-gold alloy, for example) and a magnetic property lower than those of platinum-tungsten alloys.

The indicator part 12 may be formed by bending the line body 11 comprising a titanium alloy in a predetermined shape. In this manner, various shapes indicating a wide variety of information, such as a shape surrounding cancer tissue and the like, can be formed relatively easily.

The indicator part 12 may have a shape satisfying the relationship of R>50×W/εl where R [mm] denotes a radius of curvature of the bent portion of the line body 11, W [mm] denotes a dimension of the line body 11 in the direction of the radius of curvature, and εl [%] denotes an elastic limit of the titanium alloy constituting the line body 11. This allows the indicator part 12 to be deformed into a generally linear shape within a range of elastic deformation and to be returned later to its original shape by the restoring force of elastic deformation. Thus, a degree of invasiveness when the indicator part 12 is inserted into the living body 100 can be reduced without using a nickel-titanium-based shape memory alloy or the like.

The indicator part 12 may be formed in an unclosed ring shape or in a helical shape capable of surrounding a circular region having a diameter of not smaller than 3 mm and not larger than 10 mm. This allows the indicator part 12 to appropriately surround a predetermined site in the living body 100 while making the indicator part 12 easily deformable into a generally linear shape. Thus, the position and extent of the predetermined site can be identified accurately.

The marker 10 for use in a living body may include the transporting part 14 formed by the line body 11 having a generally linear shape, which is continuous with the indicator part 12. This allows the transporting part 14 to be held for the operation of the indicator part 12. Thus, the operation of housing the indicator part 12 into the guide part 22 and the operation of making the indicator part 12 projected from the guide part 22 can be performed easily. Moreover, the orientation of the indicator part 12 can be adjusted from the outside of the living body 100 so as to place the indicator part 12 at the predetermined site in the living body 100 in an appropriate condition.

The marker 10 for use in a living body may include the orientation indicating part 16 provided in the transporting part 14 for indicating the orientation of the indicator part 12 relative to the transporting part 14. This allows an operator to recognize the orientation of the indicator part 12 even when the indicator part 12 is being housed in the guide part 22. Thus, the indicator part 12 can be placed in the living body 100 in an appropriate condition.

The orientation indicating part 16 may be formed by bending the line body 11. This allows the orientation indicating part 16, by which the orientation of the indicator part 12 can be easily recognized, to be provided very easily.

The line body 11 may have a cross-sectional shape having a longitudinal direction. This allows the orientation of the indicator part 12 to be recognized by the cross-sectional shape of the line body 11. Thus, the configuration of the marker 10 for use in a living body can be simplified by using the cross-sectional shape of the line body 11 as the orientation indicating part 16.

The instrument set 1 for inserting a marker for use in a living body according to the present embodiment includes the marker 10 for use in a living body, and the dispenser 20 for inserting the marker 10 for use in a living body into the living body 100. The dispenser 20 includes the tubular guide part 22 that houses the indicator part 12 so as to be movable in the axial direction. Such a configuration allows the indicator part 12 to be easily placed at a predetermined site in the living body 100. Thus, the predetermined site in the living body can be identified easily and accurately.

The instrument set 1 for inserting a marker for use in a living body according to the present embodiment may include the marker 10 for use in a living body, and the dispenser 20 for inserting the marker 10 for use in a living body into the living body 100. The dispenser 20 may include the tubular guide part 22 that houses the indicator part 12 so as to be movable in the axial direction while being deformed into a generally linear shape. Such a configuration allows the indicator part 12 to be easily inserted into the living body 100 by the dispenser 20 while being deformed into a generally linear shape and then to be easily returned later to its original shape. Thus, the predetermined site in the living body can be identified easily and accurately.

The line body 11 and the guide part 22 may have shapes configured to restrict a relative rotation of the marker 10 for use in a living body and the guide part 22 about the axial direction of the guide part 22. This allows for keeping the orientation of the indicator part 12 relative to the dispenser 20 and preventing the twist of the transporting part 14 or the indicator part 12 from occurring. Thus, the operation of inserting the marker 10 for use in a living body can be facilitated.

The instrument set 1 for inserting a marker for use in a living body includes the winding jig 30 to be used for winding the line body 11 therearound to form the indicator part 12. This allows for the easy formation of the indicator part 12 having a needed size by doctor's hands, for example.

The winding jig 30 includes the guide grooves 31 to 33 configured to define the winding direction of the line body 11. This allows for the easy and highly accurate formation of the indicator part 12.

The winding jig 30 includes the plurality of guide grooves 31 to 33, and the plurality of guide grooves 31 to 33 are provided at positions to bend the line body 11 with the radii of curvature R1 to R3 different from one another, respectively. This allows the line body 11 to be bent in stages to form the indicator part 12 having the predetermined radius of curvature R in a stable manner. Moreover, different types of indicator parts 12 having different radii of curvature R can be formed with a single winding jig 30.

While the embodiments of the present invention have been described above, the marker for use in a living body and the instrument set for inserting the marker for use in a living body according to the present invention are not limited to those in the above-described embodiments. It is to be understood that various modifications can be effected without departing from the scope of the present invention. The functions and effects shown in the above-described embodiments are merely an enumeration of most preferred functions and effects derived from the present invention. The functions and effects of the present invention are not limited to those described above.

The marker for use in a living body and the instrument set for inserting the marker for use in a living body according to the present invention can be utilized in the fields of medical care and dental therapy, in particular.

The invention claimed is:

1. An instrument set comprising:

a marker having an indicator part to be placed in a living body for a predetermined period of time, the indicator part being in a predetermined shape by a line body being bent, the line body including a titanium alloy; and a winding jig configured to wind the line body therearound to form the indicator part at an outside of the living body, wherein the indicator part is configured to indicate information on the living body or information on the indicator part by a difference in an X-ray image, wherein the winding jig is in a columnar shape having a plurality of outer peripheral surfaces with different outer diameters, and the winding jig includes a plurality of guide grooves formed at the plurality of outer peripheral surfaces, and the plurality of guide grooves is configured to define a winding direction of the line body by bending the line body with radii of curvature different from one another.

2. The instrument set according to claim 1, wherein at least a part of the indicator part is constituted by the titanium alloy that has an X-ray absorptivity higher than that of a stainless steel and a magnetic property lower than that of a platinum-tungsten alloy.

3. The instrument set according to claim 1, wherein the titanium alloy has an elastic limit of not lower than 2% and not higher than 6%.

4. The instrument set according to claim 1, wherein the titanium alloy contains tantalum.

* * * * *